(12) United States Patent
Johansson et al.

(10) Patent No.: US 11,712,108 B2
(45) Date of Patent: Aug. 1, 2023

(54) ORAL CARE PROCESS

(71) Applicant: Colgate-Palmolive Company, New York, NY (US)

(72) Inventors: Patrik Johansson, Hoboken, NJ (US); Leighton Davies-Smith, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 17/574,269

(22) Filed: Jan. 12, 2022

(65) Prior Publication Data
US 2022/0133028 A1 May 5, 2022

Related U.S. Application Data

(62) Division of application No. 16/436,172, filed on Jun. 10, 2019, now Pat. No. 11,241,084.
(Continued)

(51) Int. Cl.
*A61C 17/22* (2006.01)
*A46B 15/00* (2006.01)
(Continued)

(52) U.S. Cl.
CPC ...... *A46B 15/0022* (2013.01); *A46B 15/0024* (2013.01); *A46B 11/002* (2013.01);
(Continued)

(58) Field of Classification Search
CPC . A46B 15/00; A46B 15/0022; A46B 15/0024; A61C 17/22
See application file for complete search history.

(56) References Cited

U.S. PATENT DOCUMENTS

| 3,520,297 A | 7/1970 | Bechtold |
| 4,969,868 A | 11/1990 | Wang |
(Continued)

FOREIGN PATENT DOCUMENTS

| CA | 2154860 | 1/1996 |
| CN | 200953928 | 10/2007 |
(Continued)

OTHER PUBLICATIONS

International Search Report of the International Searching Authority issued in International Application PCT/US2016/068691 dated Mar. 13, 2017.

*Primary Examiner* — Michael D Jennings

(57) ABSTRACT

An oral care process which includes initiating a first operational sequence which includes generating an electric potential between a first sacrificial electrode and a second sacrificial electrode, the electric potential in the first operational sequence beginning with one of a first polarity and a second polarity, stopping the first operational sequence, and commencing a second operational sequence which includes generating the electric potential between the first sacrificial electrode and the second sacrificial electrode. The electric potential in the second operational sequence may begin with the other of the first polarity and the second polarity. The electric potential may be alternated between the first polarity and the second polarity at predetermined intervals during at least one of the first operational sequence and the second operational sequence.

15 Claims, 5 Drawing Sheets

Related U.S. Application Data

(60) Provisional application No. 62/683,125, filed on Jun. 11, 2018.

(51) Int. Cl.
*A46B 11/00* (2006.01)
*A61C 17/32* (2006.01)

(52) U.S. Cl.
CPC ..... *A46B 2200/1066* (2013.01); *A61C 17/221* (2013.01); *A61C 17/222* (2013.01); *A61C 17/32* (2013.01)

(56) References Cited

U.S. PATENT DOCUMENTS

| | | | |
|---|---|---|---|
| 5,372,501 | A | 12/1994 | Shalvi |
| 5,824,292 | A | 10/1998 | Carr et al. |
| 5,921,251 | A | 7/1999 | Joshi |
| 6,135,126 | A | 10/2000 | Joshi |
| 6,341,400 | B1 | 1/2002 | Kobayashi et al. |
| 6,955,538 | B1 | 10/2005 | Borch et al. |
| 7,479,133 | B2 | 1/2009 | Sun et al. |
| 7,775,795 | B2 | 8/2010 | Khawaled et al. |
| 7,857,620 | B2 | 12/2010 | Shih |
| 7,886,398 | B2 | 2/2011 | Morita et al. |
| 7,975,341 | B2 | 7/2011 | Cai et al. |
| 8,156,602 | B2 | 4/2012 | Jimenez et al. |
| 8,295,923 | B2 | 10/2012 | Eischen et al. |
| 8,595,882 | B2 | 12/2013 | Bax et al. |
| 8,668,397 | B2 | 3/2014 | Barkhordar |
| 8,708,700 | B2 | 4/2014 | Jimenez et al. |
| 8,734,421 | B2 | 5/2014 | Sun et al. |
| 9,009,901 | B2 * | 4/2015 | Doll ............... A46B 15/00 15/22.1 |
| 9,125,484 | B2 | 9/2015 | Gatzemeyer |
| 9,192,762 | B2 | 11/2015 | Doll et al. |
| 9,445,878 | B2 | 9/2016 | Jimenez et al. |
| 9,497,025 | B2 | 11/2016 | Alsup |
| 9,597,496 | B1 * | 3/2017 | Johansson .......... A46B 15/0022 |
| 10,179,038 | B2 * | 1/2019 | Johansson ........... A61C 19/066 |
| 2007/0071541 | A1 | 3/2007 | Vila |
| 2009/0070949 | A1 | 3/2009 | Sagel et al. |
| 2011/0304194 | A1 | 12/2011 | Uchida et al. |
| 2012/0096657 | A1 | 4/2012 | So et al. |
| 2012/0233790 | A1 | 9/2012 | Uchida et al. |
| 2013/0224679 | A1 | 8/2013 | Teggatz et al. |
| 2014/0245553 | A1 | 9/2014 | Gravina |
| 2015/0105712 | A1 | 4/2015 | Pongpeerapat |
| 2016/0184065 | A1 | 6/2016 | Johansson et al. |
| 2016/0354188 | A1 | 12/2016 | Jimenez et al. |
| 2017/0189152 | A1 * | 7/2017 | Johansson ................. C25B 1/00 |
| 2018/0369566 | A1 * | 12/2018 | Wainless ............ A46B 15/0022 |
| 2019/0008271 | A1 | 1/2019 | Gontarz et al. |
| 2019/0110876 | A1 | 4/2019 | Johansson et al. |
| 2019/0374017 | A1 | 12/2019 | Johansson et al. |

FOREIGN PATENT DOCUMENTS

| | | |
|---|---|---|
| DE | 102005009958 | 1/2007 |
| EP | 1508323 | 2/2005 |
| JP | 2009-045202 | 3/2009 |
| WO | 1990/009206 | 8/1990 |
| WO | 2001/030198 | 5/2001 |
| WO | 2007/047568 | 4/2007 |
| WO | 2009/066647 | 5/2009 |
| WO | 2009/148442 | 12/2009 |
| WO | 2013/141359 | 9/2013 |
| WO | 2016/087675 | 6/2016 |
| WO | 2016/106223 | 6/2016 |
| WO | 2017/116400 | 7/2017 |
| WO | 2017/117115 | 7/2017 |

* cited by examiner

ORAL CARE PROCESS

CROSS-REFERENCE TO RELATED APPLICATIONS

The present application is a divisional of U.S. patent application Ser. No. 16/436,172, filed Jun. 10, 2019, which claims priority to U.S. Provisional Patent Application Ser. No. 62/683,125, filed on Jun. 11, 2018, the entireties of which are incorporated herein by reference.

BACKGROUND

Oral care devices are known which provide oral health benefits through the release of ions from sacrificial electrodes. By their very nature, however, sacrificial electrodes have a limited lifespan because electrode material is lost by the production of ions during operation.

Another potential problem exhibited by sacrificial electrodes is passivation, which occurs over time simply by operating the sacrificial electrode as the anode. During such operation, a zinc oxide layer may form on the sacrificial electrode rather quickly, and this layer acts as an insulating layer that prevents the sacrificial electrode from further releasing zinc ions.

In view of the limited lifespan of sacrificial electrodes in oral care devices and the problem with passivation, there is a need for improvements to such oral care devices, and the processes by which they operate, in order to extend the lifespan of the sacrificial electrodes, limit the problem of passivation, and thereby introduce cost efficiencies.

BRIEF SUMMARY

Exemplary embodiments according to the present disclosure are directed to an oral care device that includes sacrificial electrodes for purposes of introducing beneficial ions into the oral cavity when the oral care device is used. Particularly, the oral care device includes a controller which controls the polarity of an electric potential between the sacrificial electrodes in order to extend the operational lives of the sacrificial electrodes. The polarity of the electric potential may be controlled during a single oral care session, across multiple oral care sessions, or a combination of both. Exemplary embodiments according to the present disclosure also include a method of controlling sacrificial electrodes within an oral care device in order to introduce beneficial ions into the oral cavity. The method of control advantageously leads to extending the operational lives of the sacrificial electrodes, reducing problems associated with electrode passivation, and introduces cost efficiencies.

In one aspect, the invention can be an oral care device which includes: a body including a head; a plurality of teeth cleaning elements extending from the head; a first sacrificial electrode on the head; a second sacrificial electrode on the head and spaced apart from the first sacrificial electrode; a power source; and a controller configured to alternate between an ON state and an OFF state, wherein: in the ON state the controller operably couples the power source to the first and second sacrificial electrodes to create an electric potential between the first sacrificial electrode and the second sacrificial electrode, the electric potential having one of a positive polarity and a negative polarity, and for each successive transition from the OFF state to the ON state, the controller is configured to alternate between the positive polarity and the negative polarity.

In another aspect, the invention can be an oral care method which includes: commencing a first operational sequence of an oral care device including a head, the first operational sequence including: generating an electric potential between a first sacrificial electrode and a second sacrificial electrode, the electric potential in the first operational sequence beginning with one of a positive polarity and a negative polarity, the first and second sacrificial electrodes being on the head and positioned spaced apart from each other; stopping the first operational sequence; and commencing a second operational sequence of the oral care device, the second operational sequence including: generating the electric potential between the first sacrificial electrode and the second sacrificial electrode, the electric potential in the second operational sequence beginning with the other of the first polarity and the second polarity.

In still another aspect, the invention can be an oral care device which includes: a body including a head; a plurality of teeth cleaning elements extending from the head; a first sacrificial electrode on the head; a second sacrificial electrode on the head and spaced apart from the first sacrificial electrode; a power source; and a controller configured to operably couple the power source to the first and second sacrificial electrodes to create an electric potential between the first sacrificial electrode and the second sacrificial electrode, the electric potential having one of a first polarity and a second polarity; wherein the controller is configured to switch the electric potential between the first polarity and the second polarity following a time interval which is less than an average user brushing period.

In yet another aspect, the invention can be an oral care method which includes: generating an electric potential between a first sacrificial electrode and a second sacrificial electrode, the electric potential beginning with one of a first polarity and a second polarity, the first and second sacrificial electrodes being on a head of an oral care device and positioned spaced apart from each other; and alternating the electric potential between the first polarity and the second polarity following a time interval which is less than an average user brushing period.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION

Figure 1:
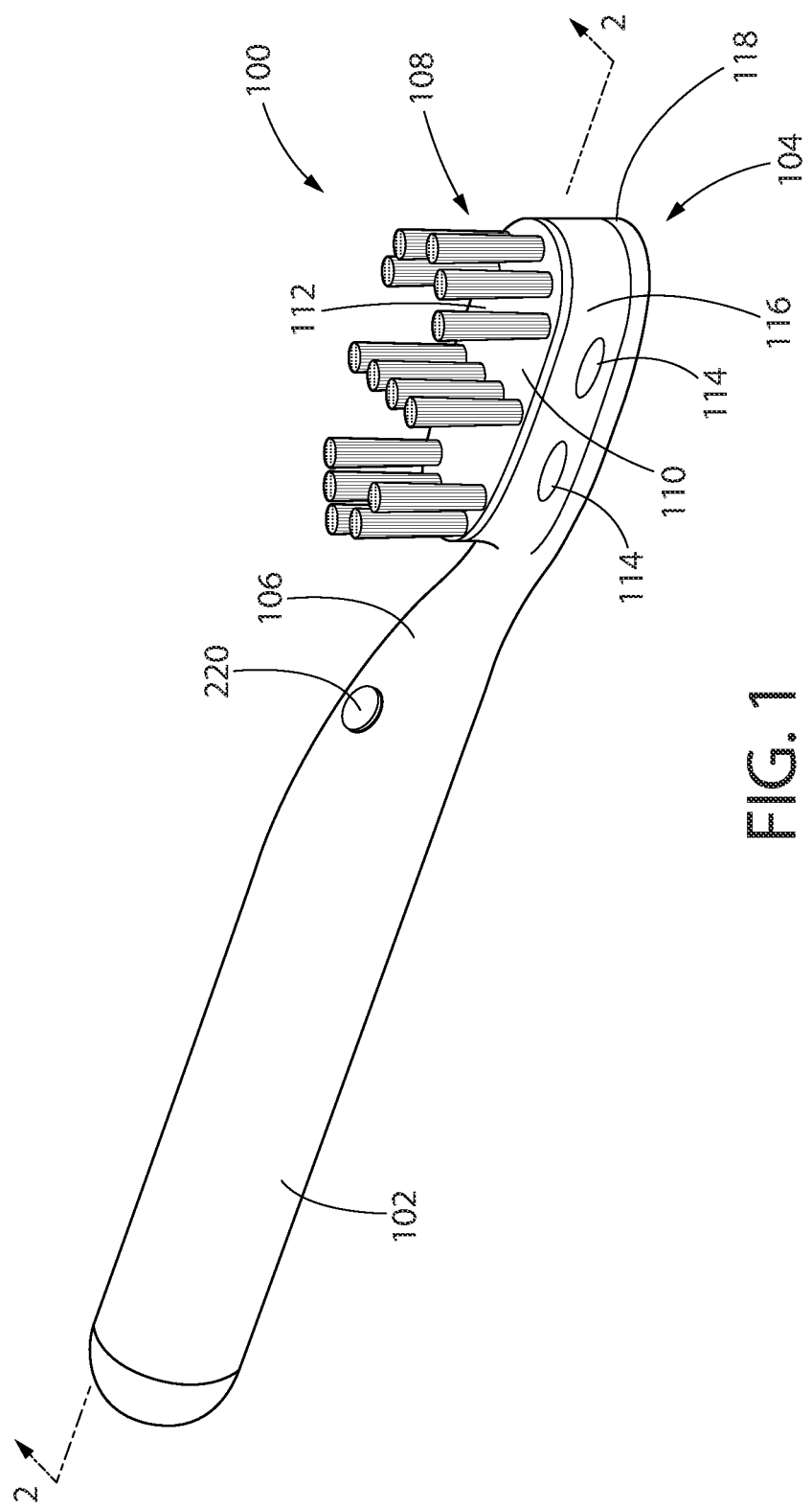
FIG. 1 is a perspective view of an oral care device including sacrificial electrodes in accordance with a first embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Turning in detail to the drawings, FIG. 1 illustrates an oral care device as a toothbrush 100 in accordance with an exemplary embodiment. The toothbrush 100 includes a handle 102, a head 104 disposed at the distal end of the handle 102, and a neck portion 106 disposed between the handle 102 and the head 104. The handle 102 has a generally elongate shape, along a longitudinal axis. In alternative embodiments, one or more of the handle 102, the head 104, and/or the neck 106 may have different shapes, sizes, orientations, and/or the like. The invention is not to be limited by the size and/or shape of any portion of the toothbrush 100 unless otherwise indicated in the claims. Additional features may also be incorporated into the toothbrush or disposed on the toothbrush. In other embodiments, the oral care device may be a toothbrush which includes a head that detaches from the handle, such that the head is replaceable with another head. In still other embodiments, the oral care device may be any other type of oral care implement.

In the embodiment illustrated in FIG. 1, the head 106 of the toothbrush 100 also includes a plurality of teeth cleaning elements 108 extend from a support plate 110. As used herein, the term "teeth cleaning elements" includes any type of structure that is commonly used for or is suitable for use in providing oral health benefits (e.g., tooth cleaning, tooth polishing, tooth whitening, massaging, stimulating, etc.) by making intimate contact with portions of the teeth and/or gums. Such teeth cleaning elements include but are not limited to tufts of bristles that can be formed to have a number of different shapes, sizes, and relative configurations, massage elements, and elastomeric cleaning members that can be formed to have a number of different shapes and sizes, or a combination of both tufts of bristles and elastomeric cleaning members. The teeth cleaning elements 108 may be arranged on the support plate 110 in many configurations.

In FIG. 1, the teeth cleaning elements 108 include bristles, which may be formed as bristle tufts. The tufts may be formed with bristles of the same or different bristle materials (such as nylon bristles, spiral bristles, rubber bristles, etc.). Moreover, while the teeth cleaning elements 108 may be arranged so that they are generally perpendicular to the top surface 112 of the support plate 110, some or all of the tooth cleaning elements may be angled with respect to the top surface 112 and/or with respect to each other. When the teeth cleaning elements 108 includes bristle tufts, it is thereby possible to select the combination of bristle configurations, bristle materials, and/or bristle orientations to achieve specific intended results and operational characteristics, thus maximizing and enhancing cleaning, tooth polishing, tooth whitening, massaging, stimulation, and the like.

The teeth cleaning elements 108 may be attached to the support plate 110 by any method, conventional or otherwise. In certain embodiments, the support plate 110 may include a plurality of holes formed there through, and the teeth cleaning elements 108 may be mounted to the support plate 110 within the holes. This type of technique for mounting the teeth cleaning elements 108 to the support plate 110 is generally known as anchor free tufting (AFT). In AFT a plate (often referred to as a head plate) or membrane is created and the teeth cleaning elements (such as bristles, elastomeric elements, and combinations thereof) are positioned into the head plate so as to extend through the holes of the head plate. The free ends of the teeth cleaning elements on one side of the head plate perform the cleaning function. The ends of the teeth cleaning elements on the other side of the head plate are melted together by heat to be anchored in place. As the teeth cleaning elements are melted together, a melt matte is formed, which is a layer of plastic formed from the collective ends of the teeth cleaning elements that connects the teeth cleaning elements to one another on one side of the head plate and prevents the teeth cleaning elements from being pulled through the tuft holes.

In example shown, after the teeth cleaning elements 108 are secured to the support plate 110, the support plate 110 is secured to the head 104. Ultrasonic welding is one technique that may be used to secure the support plate 110 to the head 104, although other techniques may also be used. When the support plate 110 is coupled to the head 104, the melt matte is located between a lower surface of the support plate 110 and a floor of a basin or cavity of the head 104 in which the support plate 110 is disposed. The melt matte, which is coupled directly to and in fact forms a part of the teeth cleaning elements 108, prevents the teeth cleaning elements 108 from being pulled through the holes in the support plate 110, thus ensuring that the teeth cleaning elements 108 remain attached to the support plate 110 during use of the oral care device 100.

In other embodiments, the teeth cleaning elements 108 may be connected to the support plate 110 or a membrane later incorporated using a technique known in the art as AMR. Generally speaking, in this technique, a head plate is provided and the bristles are inserted into holes in the head plate so that free/cleaning ends of the bristles extend from the front surface of the head plate and bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some conventional applications, after formation of the melt matte, a tissue cleaner is injection molded onto the rear surface of the head plate, thereby trapping the melt matte between the tissue cleaner and the rear surface of the head plate. Other structures may be coupled to the rear surface of the head plate to trap the melt matte between the rear surface of the head plate and such structure without the structure necessarily being a tissue cleaner. For example, a structure covering the melt matte may be a plastic material that is used to form a smooth rear surface of the head, or the like. Alternatively, the structure can be molded onto the rear surface of the head plate or snap-fit (or other mechanical coupling) to the rear surface of the head plate as desired.

Of course, techniques other than AFT and AMR can be used for mounting teeth cleaning elements 108 to the support plate 110, such as widely known and used stapling/anchoring techniques or the like. In such embodiments the teeth cleaning elements 108 may be coupled directly to the support plate 110. Furthermore, in a modified version of the AFT process discussed above, the support plate 110 may be formed by positioning the teeth cleaning elements 108 within a mold, and then molding the support plate 110 around the teeth cleaning elements 108 via an injection molding process.

Moreover, in certain embodiments, various combinations of stapled, IMT, AMR, or AFT cleaning elements may be used. Alternatively, the teeth cleaning elements 108 could be mounted to tuft blocks or sections by extending through suitable openings in the tuft blocks so that the base of the teeth cleaning elements 108 is mounted within or below the tuft block. In still other embodiments, likely in which the tooth cleaning elements are not bristles, the teeth cleaning elements 108 may be molded integrally with the support plate 110.

The head 104 also includes a plurality of apertures 114 which are disposed through a sidewall 116 of the head 104 and provide a channel or passageway through the sidewall 116. Such a channel may allow for fluid communication between the inner cavity of the head 104 of the toothbrush 100 and the environment external to the head 104. The cavity, which may be bounded by the support plate 110, the sidewall 104 and a base 118, is discussed in more detail below. In certain embodiments, the head 104 may be constructed without the cavity.

Figure 2:
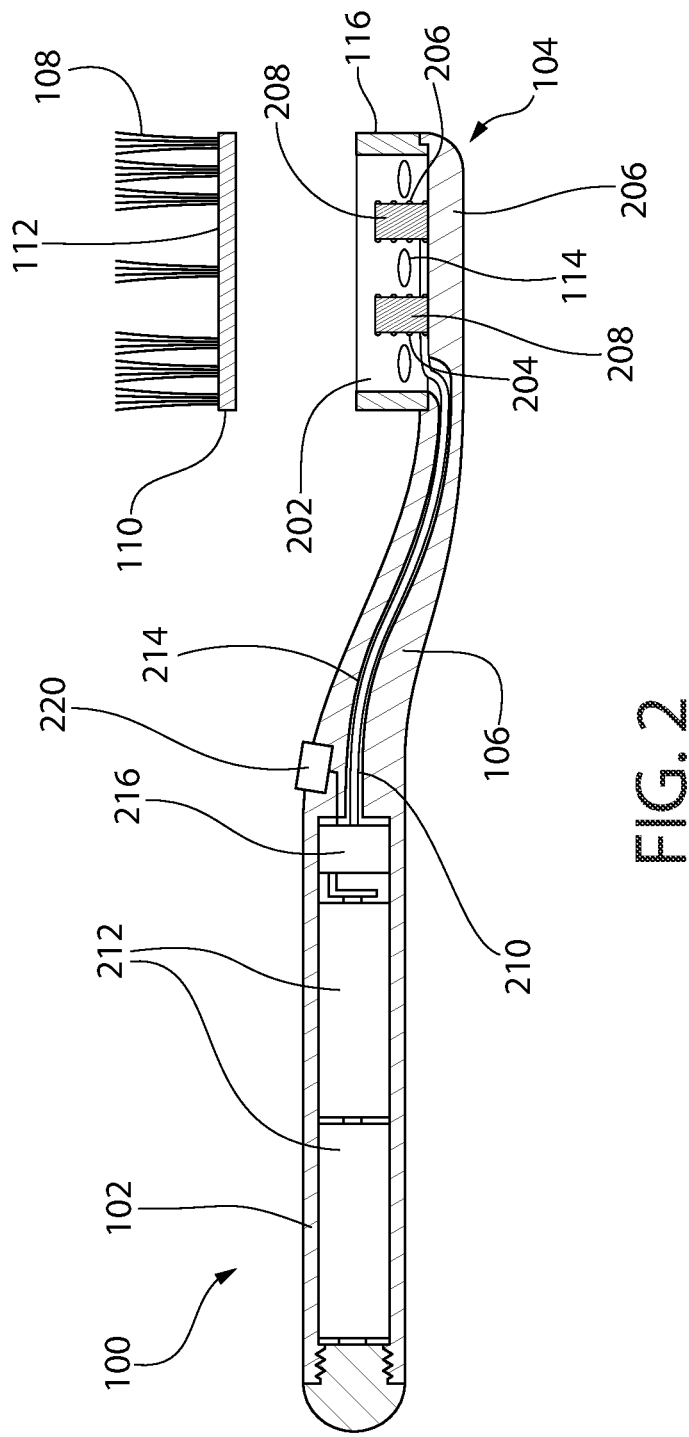
FIG. 2 is an exploded cross-sectional view of the oral care device taken along the section line A-A in FIG. 1.

FIG. 2 shows an exploded, cross-section of the toothbrush 100. In this view, the cavity 202 formed by the head 104 is shown. The cavity 202 is a basin or void defined by the sidewall 116 that extends upwardly from the base 118 of the head 104. A first sacrificial electrode 204 and a second sacrificial electrode 206 are placed on the head 104 within the cavity 202 and spaced apart from each other. The support plate 110 is positioned relative to the head 104 to cover the cavity 202, thereby enclosing the sacrificial electrodes 204, 206 in the cavity 202. In certain embodiments, the support plate 110 may be fixed at a distal end of the sidewall 116, e.g., by an adhesive, welding, or other mechanical means. In embodiments in which the head 104 does not include the cavity 202, the first and second sacrificial electrodes 204, 206 may be placed on any surface of the head 104, with the first and second sacrificial electrodes 204, 206 still positioned spaced apart from each other. In certain other embodiments, one or both of the first and second sacrificial electrodes 204, 206 may be placed on the neck portion 106 of the toothbrush 100. The invention is not to be limited by the placement of either of the first and second sacrificial electrodes 204, 206, whether on the head 104 or on the neck portion 106 of the toothbrush 100, unless otherwise expressly stated in the claims.

The sacrificial electrodes 204, 206 may be any known shape or configuration. As shown, the sacrificial electrodes 204, 206 are formed as electrical coils, and include a number of turns of a metallic wire wound about separate cores 208. The cores 208 may be formed integrally with the base or may be formed separately and subsequently fixed to the base. In other embodiments, the cores 208 may not be present at all. In other embodiments, the sacrificial electrodes 204, 206 may be formed as metal plates or other spaced-apart metal fixtures. Such other electrodes may also include zinc, zinc alloy, or some other sacrificial metal. Regardless of their shape or configuration, in certain embodiments the sacrificial electrodes 204, 206 may be formed of 90% or more of the sacrificial metal making up the electrode.

The sacrificial electrodes 204, 206 each include a sacrificial metal, and when an electric potential (i.e., a voltage difference) is generated between the first and second electrodes 204, 206, one of the sacrificial electrodes 204, 206 gives up ions, e.g., by oxidizing. In certain embodiments, the sacrificial electrodes 204, 206 includes zinc, and the presence of an electric potential oxidizes the zinc to release $Zn^{2+}$. Zinc ions are conventionally known to provide oral health benefits including, e.g., anti-bacterial benefits. In the embodiment shown in FIG. 1, zinc ions are given off in the cavity 202 of the head 104 of the toothbrush 100, and once released from the one of the sacrificial electrodes 204, 206 to the cavity 202, the beneficial zinc ions enter the oral cavity via the apertures 114.

In certain embodiments, the sacrificial electrodes 204, 206 may each include a different sacrificial metal. The sacrificial electrodes 204, 206 may be formed of materials other than zinc and zinc alloys. In certain embodiments, one or both of the sacrificial electrode 204, 206 may be formed of different metals that can be oxidized to provide ions that give alternative oral benefits. For example, Tin ions, i.e., $Sn^{2+}$ and $Sn^{4+}$, have known oral health benefits, such that one or both of the sacrificial electrodes 204, 206 could include Tin. In certain other embodiments, the oxidation of iron and/or manganese can drive the formation of hydroxide radicals from hydrogen peroxide, e.g., via the fenton reaction, which may provide other benefits in the oral cavity, such that one or both of the sacrificial electrodes 204, 206 could include iron or manganese.

The apertures 114 also allow fluids, e.g., saliva and water, in the external environment to enter the cavity 202. Once in the cavity 202, the fluids may act as an electrolyte to promote the release of the ions from the sacrificial electrodes 204, 206 upon generation of an electric potential therebetween.

Conductive leads 210 connect each of the sacrificial electrodes 204, 206 to the control circuit 216, which is in turn operably coupled to a power source 212, shown as a pair of batteries disposed in the handle 102. A switch 220 controls providing power from the power source 212 to the control circuit 216. The conductive leads 210 extend from the sacrificial electrodes 204, 206 through the neck 106 and into the handle 102 via a passageway or channel 214 connected to the cavity 202 of the head 104. The conductive leads 210 electrically couple to the control circuit 216, which controls the voltage applied from the power source 212 to the sacrificial electrodes 204, 206.

In certain embodiments, the power source 212 may be external to the toothbrush 100. In still other embodiments, the power source 212 be rechargeable batteries. In still other embodiments, the power source 212 may be any other type of power storage or power-providing electricity source which also provides a ground or negative terminal.

The control circuit 216 generates an electric potential between the two sacrificial electrodes 204, 206 by maintaining each sacrificial electrode 204, 206 at a different voltage. By doing so, one of the two sacrificial electrodes 204, 206 operates as an anode, and the other operates as a cathode. In the toothbrush 100 shown, this electric potential is created between the sacrificial electrodes 204, 206 by the control circuit 216 electrically coupling one of the sacrificial electrodes 204, 206 to the positive terminal of the power source 212 and electrically coupling the other of the sacrificial electrodes 204, 206 to the negative terminal of the power source 212.

Although one pair of electrodes is illustrated in FIG. 2, additional pairs of electrodes may also be present. For example, a first pair of sacrificial electrodes may be formed using zinc as the sacrificial metal, and a second pair of sacrificial electrodes may be formed using iron as the sacrificial metal. In such embodiments, the control circuit 216 may be used to create an electric potential between both pairs of electrodes, either simultaneously for both pair of sacrificial electrodes, or alternatively, which each pair having an electric potential between them while the other pair is decoupled from the power source 212. In other embodiments, multiple pairs of sacrificial electrodes may be included, with all the sacrificial electrodes being formed of the same sacrificial metal, with the increased number enabling for an increased release rate of ions.

Figure 3:
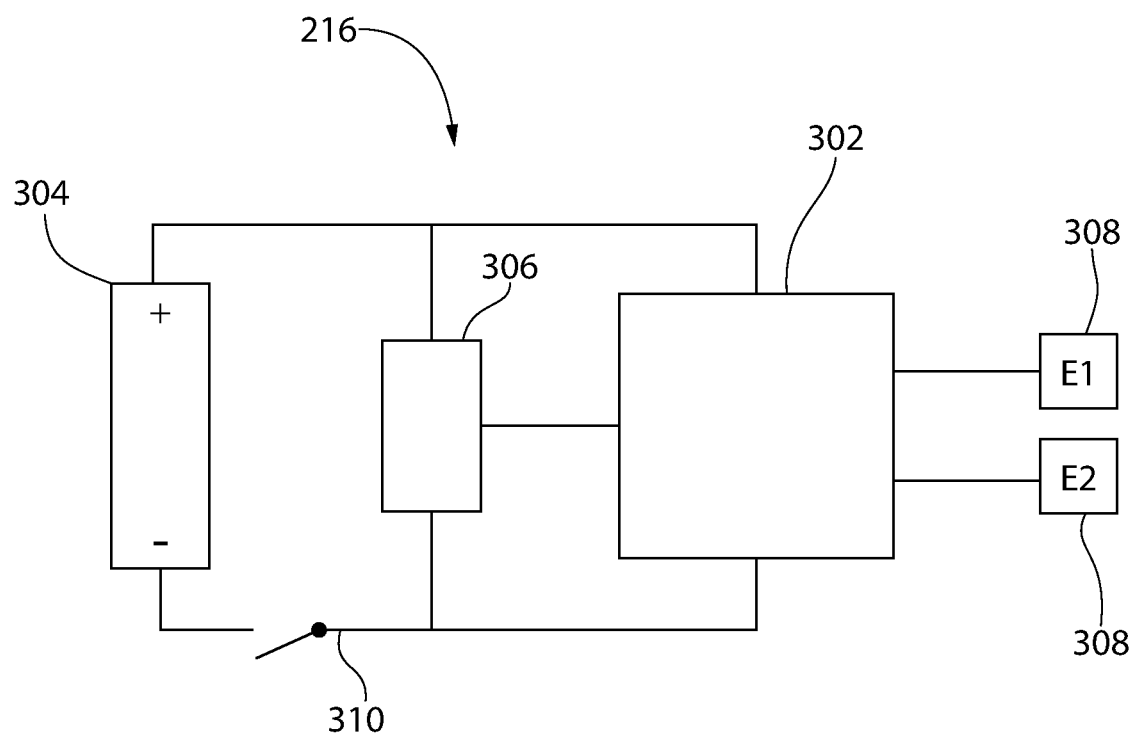
FIG. 3 is a schematic view of a control circuit for sacrificial electrodes in an oral care device.

FIG. 3 illustrates the control circuit 216 of the toothbrush 100. The control circuit 216 includes a controller 302, an oscillator 306, and a switch 310. The control circuit 216 is operably coupled to the power source 304 and to the two sacrificial electrodes 308, identified as E1 and E2. The controller 302 may be a programmable device which implements the operational features of the oral care device, as described herein, in software, hardware, firmware, or combinations thereof. In certain embodiments, the controller 302 may be implemented as an electronic sub-circuit which is assembled to perform the operational features of the oral care device as described herein.

The switch 310 operably couples the controller 302 and the oscillator 306 the power source 304. When the switch 310 is in the open position, power is not provided to the controller 302 or the oscillator 306, and the controller 302 is in the OFF state. When the switch is in the closed position, power is provided to both the controller 302 and the oscillator 306, and the controller 302 is in the ON state. When the oscillator 306 is powered, the oscillator 306 provides a clock signal to the controller 302. In certain embodiments, the oscillator 306 is a linear oscillator that produces a sinusoidal output. The output of the oscillator 306 may take any periodic waveform having a constant period, such that the constant period may be used to measure time. As described below, the controller 302 may use the clock signal as a timer to perform polarity switching for the electric potential between the sacrificial electrodes 308. In certain embodiments, the oscillator 306 may be omitted from the control circuit 216. In certain other embodiments, the oscillator 306 may be integrated as part of the controller 302.

When the controller 302 is in the ON state, the controller 302 electrically couples one of the sacrificial electrodes 308 to the positive terminal of the power source 304 and the other of the sacrificial electrodes 308 to the negative terminal of the power source 304. By coupling the sacrificial electrodes 308 to the power source 304 in this manner, an electric potential is generated between the sacrificial electrodes 308. The electric potential generated between the sacrificial electrodes 308 may have a first polarity or a second polarity. When the electric potential between the sacrificial electrodes 308 has the first polarity, one of the sacrificial electrodes 308 operates as the anode and the other operates as the cathode, and when the electric potential has the second polarity, the sacrificial electrodes 308 reverse their functions as anode and cathode. Although both electrodes 308 are formed as sacrificial electrodes, such that both are capable of releasing ions under certain conditions, only the one of the electrodes 308 operating as the anode releases ions—the other of the electrodes 308 operating as the cathode does not release ions. For purposes of convenience for this description, the first polarity is a positive polarity and the second polarity is a negative polarity, although in certain embodiments the first polarity may be a negative polarity and the second polarity may be a positive polarity. In this context, and again for purposes of this description, an electric potential with a positive polarity is generated by the control circuit 216 of FIG. 3 when the sacrificial electrode E1 is electrically coupled to the positive terminal of the power source 304 and the sacrificial electrode E2 is electrically coupled to the negative terminal of the power source 304. Likewise, an electric potential with a negative polarity is generated by the control circuit of FIG. 3 when the sacrificial electrode E1 is electrically coupled to the negative terminal of the power source 304 and the sacrificial electrode E2 is electrically coupled to the positive terminal of the power source 304.

In certain embodiments, for each successive transition from the OFF state to the ON state, the controller 302 is configured to alternate the electric potential between the positive polarity and the negative polarity. In other words, in a first transition of the controller 302 from the OFF state to the ON state, the controller 302 generates a positive polarity between the sacrificial electrodes 308, and in an immediate subsequent transition of the controller 302 from the OFF state to the ON state, the controller 302 generates a negative polarity between the sacrificial electrodes 308.

In other embodiments, when the controller 302 is in the ON state, the controller 302 is configured to switch the electric potential between the positive polarity and the negative polarity at predetermined intervals. In such embodiments, the controller 302 measure the predetermined intervals using the clock signal, with each predetermined interval being the equivalent of a plurality of periods of the clock signal. In still other embodiments, the predetermined interval of a switch between the positive polarity and the negative polarity may be a time interval which is less than a user brushing period. In such embodiments, the time interval may be about one-half the user brushing period. In other such embodiments, the time interval may be about 30 seconds or less. In still other such embodiments, the time interval may be about 15 seconds or less. In still other embodiments, the time interval may be any value between about 1 second and the end of the user brushing period, and such a value for the time interval may be predetermined, such that it is set before the toothbrush is used by the user.

In certain embodiments, the user brushing period may be a predetermined time period that is set before the toothbrush is used by the user. For example, in certain embodiments, the user brushing period may be set to a time period of two minutes, which is the brushing time that is generally recommended by oral health care professionals when practicing good oral hygiene. In certain other embodiments, the user brushing period may be set to a time period of less than the generally recommended bushing time of two minutes. In such embodiments, the user brushing period may be set to any time period in the range of 1 second to two minutes, as predetermined before the toothbrush is used by the user. By way of example, the user brushing period may be set to a time period in the range of 1 second to two minutes based on the experience and knowledge of a designer, engineer, or the like at the time of manufacture. By way of another example, the user brushing period may be set to a time period based on a collection of sample data. In such embodiments, the user brushing period may be set to the average brushing period as determined by the collected sample data.

Figure 4:
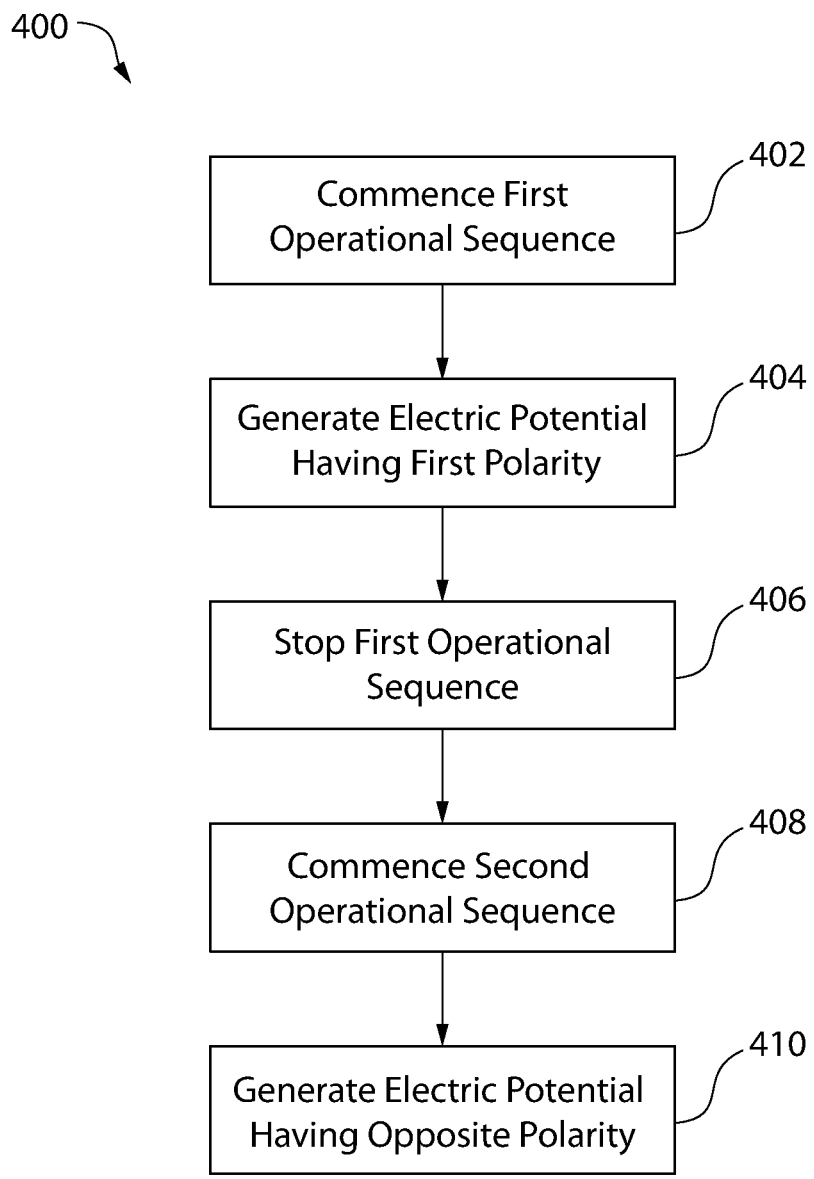
FIG. 4 is a flowchart showing a first operating process for an oral care device including sacrificial electrodes.

FIG. 4 is a flowchart showing an operational process 400 that may be implemented with the control circuit 216. In the first step 402, the control circuit commences a first operational sequence, and in the second step 404, the controller transitions from the OFF state to the ON state so that an electrical potential is generated between the sacrificial electrodes. The electrical potential in this first operational sequence may have a positive polarity or a negative polarity. In certain embodiments during the first operational sequence, the controller may alternate the electric potential between the positive polarity and the negative polarity. In such embodiments, alternating between the positive polarity and the negative polarity may occur at predetermined intervals as described above. In the third step 406, the first operational sequence ends with the controller transitioning to the OFF state. In the fourth step, 408, the control circuit commences a second operational sequence, and in the fifth step 410, the controller transitions to the ON state again so that an electrical potential is once again generated between the sacrificial electrodes. This second operational sequence ends when the controller transitions once again to the OFF state. The electrical potential in this second operational sequence may have a positive polarity or a negative polarity, dependent upon the initial polarity in the first operational sequence. If the first operational sequence initially generates the electric potential with a positive polarity, then the second operational sequence initially generates the electric potential with a negative polarity. Similarly, if the first operational sequence initially generates the electric potential with a negative polarity, then the second operational sequence initially generates the electric potential with a positive polarity.

In certain embodiments during the second operational sequence, the controller may alternate the electric potential between the positive polarity and the negative polarity. In such embodiments, alternating between the positive polarity and the negative polarity may occur at predetermined intervals as described above. In still other embodiments, during the first operational sequence, the controller initially generates the electric potential having one of the positive polarity and the negative polarity, and during the second operational sequence, the controller initially generates the electric potential having the other of the positive polarity and the negative polarity.

Figure 5:
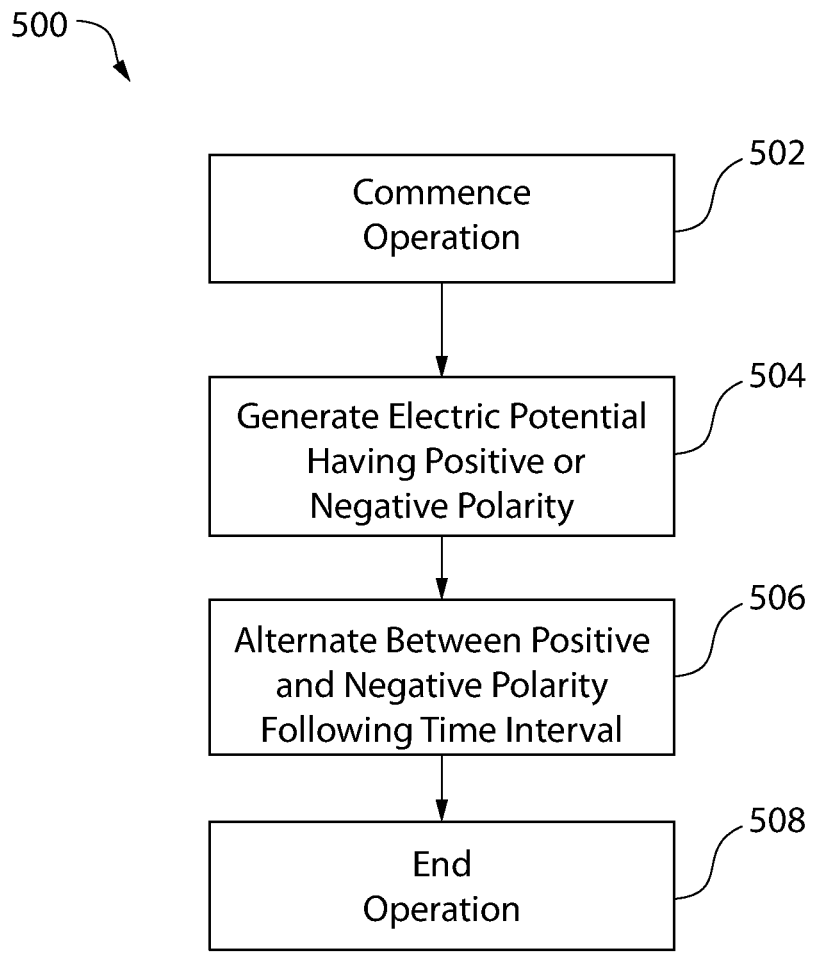
FIG. 5 is a flowchart showing a second operating process for an oral care device including sacrificial electrodes.

FIG. 5 is a flowchart showing an operational process 500 that may be implemented with the control circuit 216. In the first step 502, the control circuit commences operation, and in the second step 504, the controller transitions from the OFF state to the ON state so that an electrical potential is generated between the sacrificial electrodes. In this second step 504, the electrical potential has either a positive polarity or a negative polarity. In the third step 506, the electrical potential is alternated between the positive polarity and the negative polarity following a time interval which is less than an average user brushing period. As described above, the time interval may be half of the average user brushing period, it may be 30 seconds or less, or it may be 15 seconds or less. In the last step 508, the control circuit ends operation when the controller transitions from the ON state to the OFF state.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care process comprising:
   commencing a first operational sequence of an oral care device, the first operational sequence comprising:
      generating an electric potential between a first sacrificial electrode and a second sacrificial electrode, the electric potential in the first operational sequence beginning with one of a first polarity and a second polarity;
   stopping the first operational sequence; and
   commencing a second operational sequence of the oral care device, the second operational sequence comprising:
      generating the electric potential between the first sacrificial electrode and the second sacrificial electrode, the electric potential in the second operational sequence beginning with the other of the first polarity and the second polarity.

2. The oral care process of claim 1, wherein during at least one of the first operational sequence and the second operational sequence, the electric potential is alternated between the first polarity and the second polarity at predetermined intervals.

3. The oral care process of claim 1, wherein one of the first sacrificial electrode and the second sacrificial electrode gives off ions in response to the electric potential.

4. The oral care process of claim 1, wherein each of the first sacrificial electrode and the second sacrificial electrode comprises zinc.

5. The oral care process of claim 1 wherein the first and second sacrificial electrodes are positioned on the oral care device in a spaced apart manner.

6. The oral care process of claim 5 wherein the first and second sacrificial electrodes are located on a head of the oral care device.

7. An oral care process comprising:
generating an electric potential between a first sacrificial electrode and a second sacrificial electrode, the electric potential beginning with one of a first polarity and a second polarity; and
alternating the electric potential between the first polarity and the second polarity following a time interval which is less than two minutes.

8. The oral care process of claim 7, wherein the time interval is one minute or less.

9. The oral care process of claim 7, wherein the time interval is 30 seconds or less.

10. The oral care process of claim 7, wherein the time interval is 15 seconds or less.

11. The oral care process of claim 7, wherein the time interval is a plurality of periods of a clock signal generated by an oscillator.

12. The oral care process of claim 7, wherein one of the first sacrificial electrode and the second sacrificial electrode gives off ions in response to the electric potential.

13. The oral care process of claim 7, wherein each of the first sacrificial electrode and the second sacrificial electrode comprises zinc.

14. The oral care process of claim 7 wherein the first and second sacrificial electrodes are located on a head of an oral care device.

15. The oral care process of claim 14 wherein the first and second sacrificial electrodes are positioned spaced apart from each other.

* * * * *